(12) United States Patent
Park et al.

(10) Patent No.: US 11,986,676 B2
(45) Date of Patent: May 21, 2024

(54) LOW ENERGY RADIATION THERAPY SYSTEM FOR SUPERFICIAL LESION TREATMENT AND OPERATION METHOD THEREOF

(71) Applicant: KOREA INSTITUTE OF RADIOLOGICAL & MEDICAL SCIENCES, Seoul (KR)

(72) Inventors: Seung Woo Park, Seoul (KR); Su Chul Han, Seoul (KR); Jong Hyun Baek, Changwon (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 481 days.

(21) Appl. No.: 17/428,920

(22) PCT Filed: Jan. 29, 2020

(86) PCT No.: PCT/KR2020/001363
§ 371 (c)(1),
(2) Date: Aug. 5, 2021

(87) PCT Pub. No.: WO2020/162672
PCT Pub. Date: Aug. 13, 2020

(65) Prior Publication Data
US 2022/0126118 A1      Apr. 28, 2022

(30) Foreign Application Priority Data

Feb. 8, 2019  (KR) .................. 10-2019-0015137

(51) Int. Cl.
*A61N 5/10*      (2006.01)
*B22F 10/80*     (2021.01)
*B33Y 50/00*     (2015.01)

(52) U.S. Cl.
CPC ............ *A61N 5/1065* (2013.01); *A61N 5/103* (2013.01); *A61N 5/1071* (2013.01); *B22F 10/80* (2021.01);
(Continued)

(58) Field of Classification Search
CPC .... A61N 5/1028; A61N 5/103; A61N 5/1065; A61N 5/1071; A61N 2005/1057;
(Continued)

(56) References Cited

FOREIGN PATENT DOCUMENTS

| CN | 105664377 B | 6/2018 |
|---|---|---|
| JP | 2008011963 A | 1/2008 |

(Continued)

OTHER PUBLICATIONS

The Extended European Search Report for European Patent Application No. 20751946.3, dated Sep. 29, 2022.

*Primary Examiner* — Mark R Gaworecki

(57) ABSTRACT

The present invention relates to a low energy radiation therapy system for superficial lesion treatment and an operation method thereof, the low energy radiation therapy system comprising: an optical scanner for acquiring 3D scanning data of a treatment region including a superficial lesion site; an irradiation unit configured to apply radiation to the treatment region; a calculation unit for calculating, on the basis of the 3D scanning data, a skin dose, energy of radiation, and a part-specific radiation amount adjustment value, and producing, according to the part-specific radiation amount adjustment value, shape data of a compensation unit to be provided at the end of the irradiation unit; and a 3D printer configured to three-dimensionally print and produce the compensation unit according to the shape data.

10 Claims, 14 Drawing Sheets

(52) U.S. Cl.
CPC ............ *B33Y 50/00* (2014.12); *A61N 5/1028* (2013.01); *A61N 2005/1059* (2013.01); *A61N 2005/1091* (2013.01); *A61N 2005/1095* (2013.01); *A61N 2005/1096* (2013.01); *Y02P 10/25* (2015.11)

(58) Field of Classification Search
CPC .... A61N 2005/1059; A61N 2005/1091; A61N 2005/1095; B22F 10/80; B33Y 50/00; Y02P 10/25
See application file for complete search history.

(56) References Cited

FOREIGN PATENT DOCUMENTS

| | | | | |
|---|---|---|---|---|
| KR | 20140057916 | A | 5/2014 | |
| KR | 101721798 | B1 | 3/2017 | |
| KR | 101739690 | B1 | 5/2017 | |
| KR | 20180010758 | A | 1/2018 | |
| WO | 2015/077881 | A1 | 6/2015 | |
| WO | WO-2015077881 | A1 * | 6/2015 | ............ A61B 6/032 |
| WO | 2015101678 | A2 | 7/2015 | |

* cited by examiner

LOW ENERGY RADIATION THERAPY SYSTEM FOR SUPERFICIAL LESION TREATMENT AND OPERATION METHOD THEREOF

TECHNICAL FIELD

The disclosure relates to a low-energy radiation therapy system for superficial lesion treatment and an operation method thereof, and more particularly to a low-energy radiation therapy system in which a radiation dose is adjusted according to regions to treat a lesion having an uneven surface the radiation dose.

BACKGROUND ART

Due to recent environmental pollution, aging, etc., skin diseases, basal cell carcinoma, squamous cell carcinoma, and the like diseases have been on the rise. Such diseases occur in skin. Because the surface of a body has the diseases, the diseases frequently occur on a curved surface and are generally developed in an irregular shape. To treat the foregoing superficial lesions, a laser and a surgical operation have been employed. In particular, to treat skin cancer, an electron beam based on a high-energy linear accelerator has been used for the purpose of cancer treatment. Besides, there has been used the Mohs micrographic surgery, but a medical specialist needs to additionally have experience and knowledge about the Mohs micrographic surgery and a patient and a doctor are increased in fatigue because the surgery takes a long time.

As a treatment method of using the electron beam based on the high-energy linear accelerator, PCT publication No. WO2015/101678 has been disclosed.

However, such a related art has a problem of difficulty in making a treatment region including an uneven surface be uniformly irradiated with a radiation dose.

DISCLOSURE

Technical Problem

The disclosure is conceived to solve conventional problems, and an aspect of the disclosure is to provide an irradiation system for making an uneven the lesion part be uniformly irradiated with a radiation dose and an operation method thereof.

Technical Solution

To achieve the aspect of the disclosure, there is provided a low-energy radiation therapy system for superficial lesion treatment, including: an optical scanner configured to obtain 3D scanning data of a treatment region including a superficial lesion part; an irradiation unit configured to emit radiation to the treatment region; a calculator configured to calculate a skin dose, energy of the radiation, and adjustment values for radiation doses according to parts based on the 3D scanning data, and generate shape data about a compensation unit provided in an end portion of the irradiation unit based on the adjustment values for the radiation doses according to the parts; and a 3D printer configured to perform 3D printing based on the shape data to make the compensation unit.

Meanwhile, the calculator may be configured to generate the shape data about the compensation unit so that a skin dose of the lesion part can be uniformized in a state that the compensation unit is spaced part from the lesion part.

Meanwhile, the irradiation unit may be configured to adjust the energy of the radiation.

Further, the irradiation unit may be configured to vary within a range of 100 to 225 KV.

Meanwhile, the calculator may be configured to calculate a distance from a skin surface to an end of the irradiation unit based on the skin dose and the energy of the radiation.

Meanwhile, the low-energy radiation therapy system may further include a monitor configured to monitor the skin dose when the compensation unit is applied to the irradiation unit.

Further, the calculator is configured to generate the shape data so that the skin dose in the lesion part can converge into a predetermined range based on a minimum value of the skin dose.

Meanwhile, the irradiation unit may be configured to emit an X-ray.

Here, the calculator may be configured to extract the 3D scanning data from an image obtained by scanning the lesion part through the optical scanner.

Meanwhile, the superficial lesion part may include skin cancer.

In addition, there is provided an operation method of a low-energy radiation therapy system for superficial lesion treatment, the operation method including: setting a reference position as a scanning position of a scanner to scan a skin surface including a superficial lesion part; obtaining 3D scanning data about a treatment region by the scanner; calculating skin doses according to parts of the treatment region based on the 3D scanning data; calculating adjustment values for radiation doses according to parts based on the skin doses according to parts; calculating shape data about a compensation unit based on the 3D scanning data and the adjustment values for the radiation doses according to parts; printing the compensation unit by a 3D printer; and emitting an X-ray to the treatment region at the reference position by an irradiation unit mounted with the compensation unit.

The operation method may further include performing monitoring by emitting the X-ray in a state that the compensation unit is mounted to the irradiation unit and measuring a radiation dose after the printing.

Advantageous Effects

According to the disclosure, a low-energy radiation therapy system for superficial lesion treatment and an operation method thereof are improved in accuracy because an uneven superficial lesion part is uniformly irradiated with a radiation dose, and make it possible to rapidly carry out the treatment because time taken from scanning to final irradiation is shortened. Further, a structure for shielding radiation is minimized because low energy is used in the treatment.

MODE FOR CARRYING OUT DISCLOSURE

Figure 1:
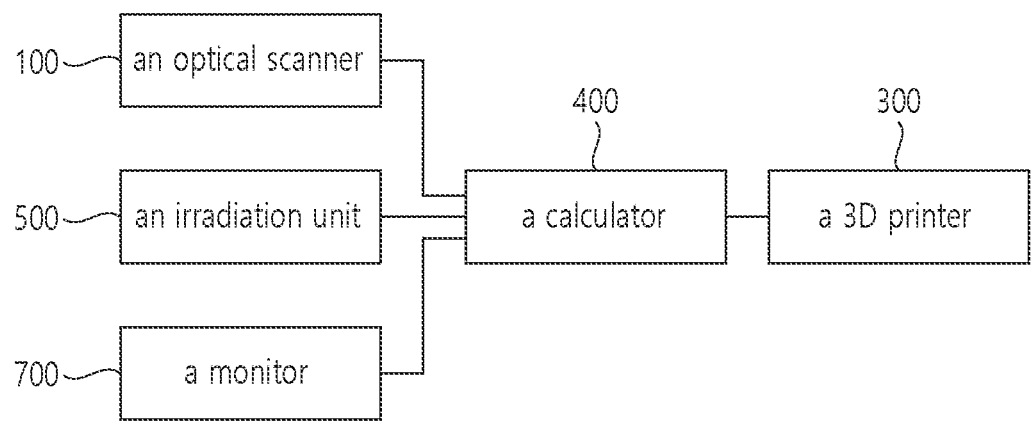
FIG. 1 is a block diagram showing concept of an irradiation system according to the disclosure.

Below, a low-energy radiation therapy system for superficial lesion treatment and an operation method thereof according to an embodiment of the disclosure will be described in detail with reference to the accompanying drawings. Elements described in the following embodiments may be called other names in relevant fields. However, if the elements are similar or identical in terms of their functions, they may be regarded as equivalents even in alternative embodiments. Further, signs assigned to the elements are given for convenience of description. However, content on the drawings with these given signs do not limit the elements to a range in the drawings. Likewise, even though the elements on the drawings are partially modified according to alternative embodiments, they having functional similarity and identity may be regarded as equivalents. Further, if those skilled in the art recognizes natural involvement of elements, descriptions of the elements will be omitted.

Meanwhile, the following descriptions will be made on the premise that a treatment region refers to a region of a predetermined range to which radiation is emitted, and a lesion part refers to a part where a lesion necessary for death of tissue occurs. Therefore, the treatment region in the following may include normal tissue and a lesion part.

FIG. 1 is a block diagram showing concept of an irradiation system according to the disclosure, and FIGS. 2A, 2B, 2C and 2D are conceptual diagrams showing a structure of the irradiation system according to the disclosure.

As shown therein, a low-energy radiation therapy system for superficial lesion treatment the disclosure is configured to scan a treatment region 10, make a compensation unit 600 suitable for the lesion part 20, and perform an optimized radiation therapy.

The low-energy radiation therapy system for the superficial lesion treatment according to the disclosure may include an optical scanner 100, an irradiation unit 500, a calculator 400, a 3D printer 300 and a monitor 700.

Figure 2A:
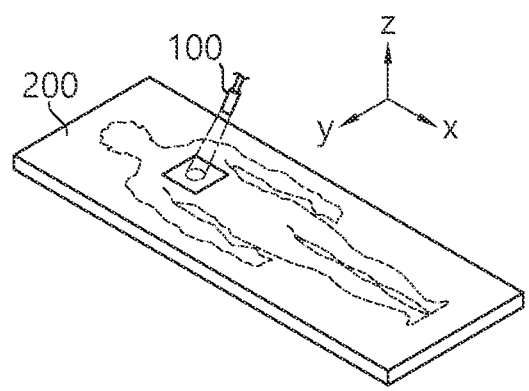
FIGS. 2A, 2B, 2C and 2D are conceptual diagrams showing a structure of the irradiation system according to the disclosure.

Referring to FIG. 2A, the optical scanner 100 is configured to obtain information about the surface of the treatment region 10. The optical scanner 100 obtains 3D scanning data by collecting optical information about the treatment region 10 on a skin surface 1 of a patient who lies on a treatment table 200 in a position at a predetermined distance from the treatment region 10. The optical information about the treatment region 10 may include a patient's body shape, unevenness of a treatment site, a shape of the lesion part 20, and the like three-dimensional (3D) information (x, y and z coordinates and a scanning direction coordinate) of the skin surface. The 3D scanning data may for example include data obtained within a visible light range.

Although it is not shown, a scanner position adjuster (not shown) may be provided to adjust the position and posture of the optical scanner 100. The scanner position adjuster may be supported at one side thereof on the ground, and provided with the optical scanner 100 at the other side thereof. The scanner position adjuster may include a plurality of links so that the optical scanner 100 can be stably positioned.

Meanwhile, the optical scanner 100 may include a plurality of sensors to provide information about a scanning position and a scanning direction. Although the same the lesion part 20 is scanned, obtained scanning data may be varied depending on the scanning positions and the scanning directions, and thus a radiation dose based on the obtained scanning data may also be varied. Therefore, the irradiation unit 500 and the optical scanner 100 are required to be set with the same position information. However, the optical scanner 100 and the irradiation unit 500 are adjustable in scale based on calculation even though their distances from the treatment region 10 are different. Accordingly, at least the scanning direction of the optical scanner 100 may be aligned with the irradiation direction of the irradiation unit 500.

However, the optical scanner 100 and the scanner position adjuster may have various structures, and thus further descriptions thereof will be omitted.

The irradiation unit 500 is configured to emit radiation to the treatment region 10 including the superficial lesion part 20. According to the disclosure, the irradiation unit 500 is configured to emit low-energy radiation. Further, the irradiation unit 500 may be configured to adjust a radiation dose for the whole region to be irradiated, and may specifically be configured to emit radiation within a range of 100 to 225 KV. For example, the irradiation unit 500 may be an X-ray tube capable of emitting an X-ray of a KV-class. The irradiation unit 500 may be connected to a link connected to a radiation-generator main body. The link may be configured to adjust the irradiation position and posture of the irradiation unit 500. Meanwhile, the compensation unit 600 to be described later is provided on the end of the irradiation unit 500 so that a radiation dose is controlled. Here, the end of the irradiation unit 500 may be formed with a mounting portion (not shown) to which the compensation unit 600 is easily attached and detached.

The calculator 400 is configured to calculate an adjustment value of a radiation dose based on physical properties or the like of the compensation unit 600 (to be described later) and 3D scanning data obtained by the optical scanner 100, and generate shape data about the compensation unit 600 based on the calculated adjustment value. The calculator 400 may include a plurality of processors, and may be configured to generate the shape data based on a preset algorithm.

Detailed functions of the calculator 400 are as follows. The calculator 400 extracts the coordinates of the lesion part 20 within a scanning area based on the 3D scanning data, and calculates a necessary skin dose at points according to unit coordinates in the lesion part 20. The necessary skin dose is minimized for normal tissue desired to be not exposed to radiation, but is set to have a value intended to cure the lesion part 20. Next, the calculator 400 calculates a radiation dose of low-energy radiation emitted from the irradiation unit 500. Here, the calculator 400 calculates the radiation dose on the assumption that the irradiation unit 500 is disposed at the same position as the optical scanner 100. Further, the calculator 400 may calculate a distance between the irradiation unit and the treatment region and a voltage for adjusting energy of an X-ray, which are required when adjustment of the radiation dose is needed throughout the treatment region, for example, when the radiation dose for the whole treatment region is increased or decreased in response to a user's input.

The calculator 400 calculates an adjustment value of the radiation dose with respect to the unit coordinates in the treatment region 10 when the radiation dose of the irradiation unit 500 and the necessary skin dose are determined. Here, the unit coordinates may for example include coordinates based on a unit distance (i.e., a step size) by which movement is allowable in very small units when the compensation unit 600 is made. Therefore, it is possible to adjust the radiation dose in units when the compensation unit 600 is made.

The calculator 400 generates shape data about the compensation unit 600 based on the adjustment value of the radiation dose. In the shape data, height may be determined based on the radiation doses which are required to be adjusted according to coordinates in a plane coordinate system corresponding to the treatment region 10. Here, the radiation dose to be adjusted may be varied depending on the materials of the compensation unit 600, and therefore the material of the compensation unit 600 may be taken into account in determining the shape data. In this regard, detailed descriptions of the calculator 400 will be made later.

Figure 2B:
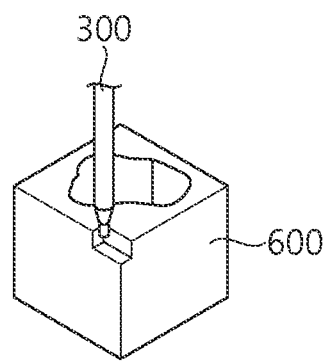

Referring to FIG. 2B, the 3D printer 300 is configured to print the compensation unit 600, which will be mounted to the end of the irradiation unit 500 based on the shape data generated by the calculator 400.

Figure 2C:
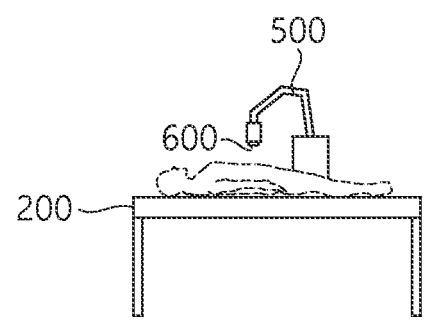
Figure 2D:
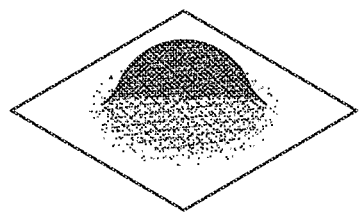

Referring to FIG. 2C, the monitor 700 is configured to measure a radiation dose based on radiation emitted in the state that the compensation unit 600 is mounted to the irradiation unit 500. Referring to FIG. 2D, the monitor 700 makes it possible to determine whether the skin doses according to the coordinates of the treatment region 10 are actually controlled as desired within a preset distance between the end portion of the irradiation unit 500 and a patient. When there is difference between a dose actually measured by the monitor 700 and the necessary skin dose, the difference may be reflected in modifying the shape data.

Below, the compensation unit 600 formed by the 3D printer 300 will be described. In the meantime, the description will be made on the premise that 'forming', 'making' or 'producing' refers to a process of forming a predetermined shape with raw materials for 3D printing.

FIGS. 3A, 3B, 3C and 3D are conceptual diagrams showing concept of making a compensation unit. As shown therein the compensation unit 600 may be formed based on the shape data obtained from a simulation result of the calculator 400.

Figure 3A:
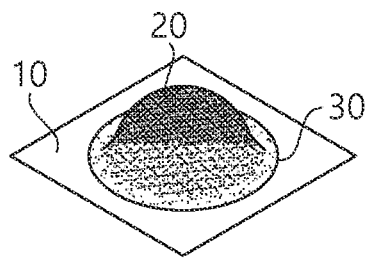
FIGS. 3A, 3B, 3C and 3D are conceptual diagrams showing concept of making a compensation unit.
Figure 3B:
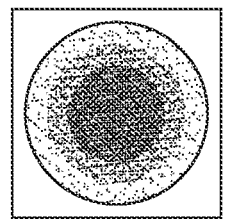
Figure 3C:
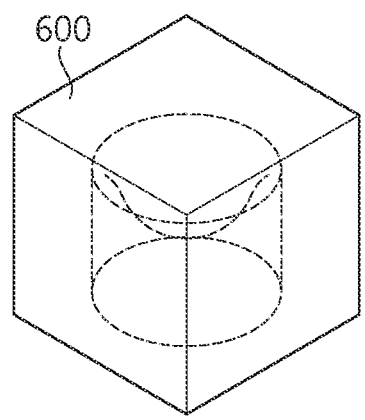
Figure 3D:
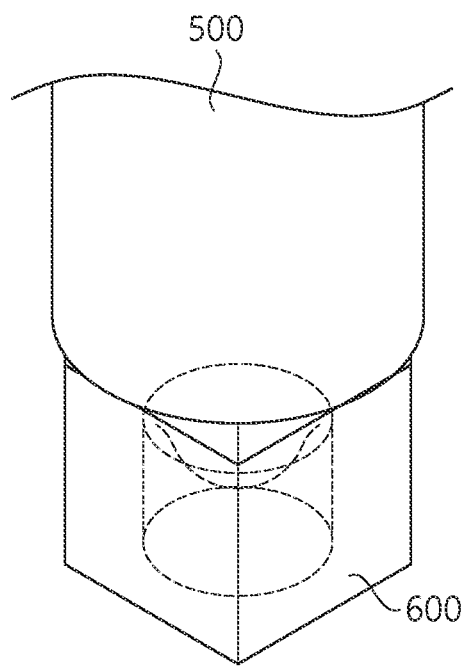

Referring to FIG. 3A, as described above, the calculator 400 calculates a necessary skin dose based on 3D scanning data. Then, referring to FIG. 3B, the calculator 400 calculates an adjustment value of a radiation dose according to the coordinates of the treatment region 10. Then, referring to FIG. 3C, the calculator 400 generates shape data about the compensation unit 600 based on the calculated adjustment value of the radiation dose. Then, referring to FIG. 3D, the compensation unit 600 is made by the 3D printing, and then mounted to the end of the irradiation unit 500, thereby finishing preparations for use.

Meanwhile, a material, which is effective in attenuating radiation, may be selected as the compensation unit 600. Here, at least a portion of the treatment region 10 is varied in the amount of attenuating the radiation, thereby adjusting the radiation dose. Parts of the compensation unit 600 are different in length of an irradiation path, and therefore the radiation dose is adjusted according to the regions.

The attenuation amount of the compensation unit 600 may be varied depending on the materials of the compensation unit 600. In this regard, when the material of the compensation unit 600 is selected, the calculator 400 may determine a shape based on the properties of the material. For example, the compensation unit 600 may be made of a material of which physical properties are similar to those of human tissue.

Meanwhile, as described above, the compensation unit 600 is mounted to the end of the irradiation unit and positioned at the start of the irradiation path, so that the compensation unit 600 cannot be in contact with the treatment region 10. Therefore, there are no limits to the property of the material, for example, biocompatibility, which is required for the compensation unit 600 if used in contact with skin. For example, the compensation unit 600 may be made of metal which is excellent in a radiation shielding effect even though a small amount of metal is used, and extendable to metal which is suitable for the 3D printing.

Below, calculation concept of the calculator 400 will be described in detail with reference to FIGS. 4 to 7. For convenience, the description will be made with reference to the cross-sections of the irradiation unit and the treatment region.

Figure 4:
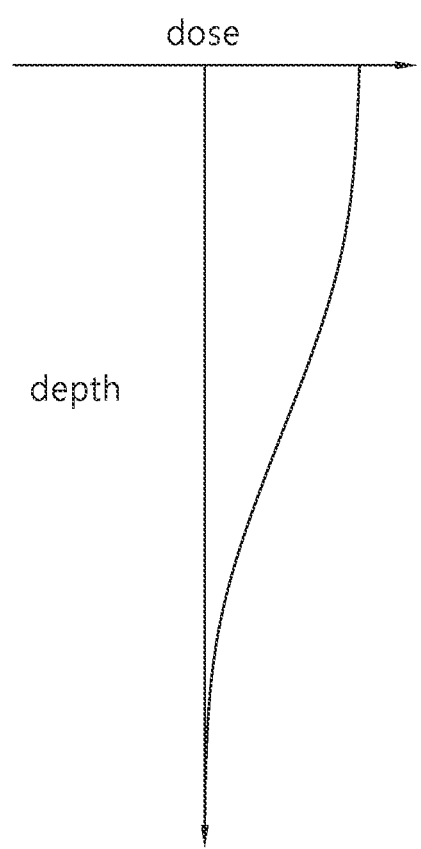
FIG. 4 illustrates a radiation dose of low-energy radiation emitted from an irradiation unit.
Figure 5:
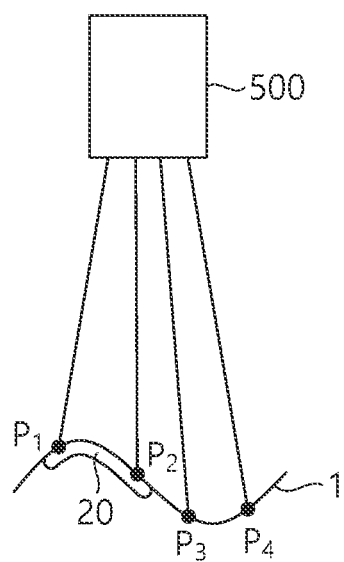
FIG. 5 is a cross-sectional view showing an example of emitting radiation without the compensation unit.
Figure 6:
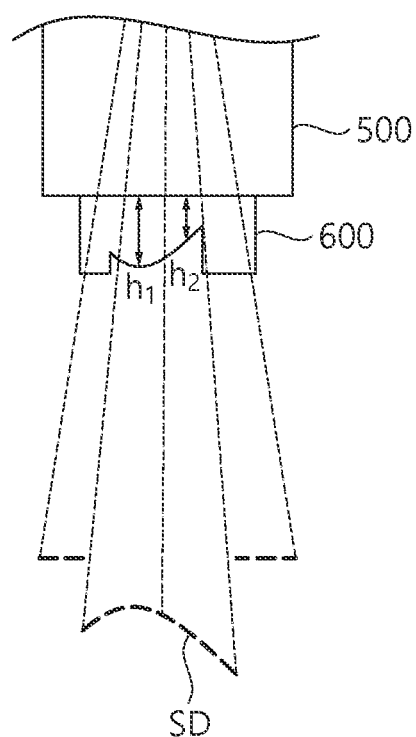
FIG. 6 is a diagram showing points where a uniform radiation dose is exhibited with the compensation unit.
Figure 7:
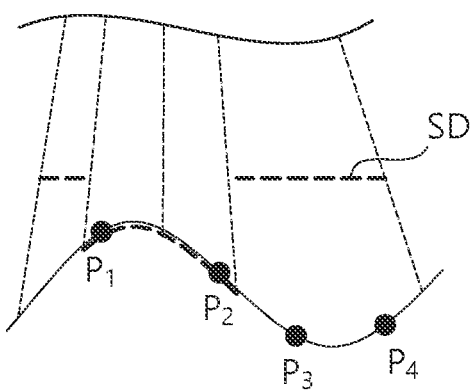
FIG. 7 is a diagram showing both the lesion part and the points uniformly irradiated with the radiation dose of FIG. 6.

FIG. 4 illustrates a radiation dose of low-energy radiation emitted from an irradiation unit, FIG. 5 is a cross-sectional view showing an example of emitting radiation without the compensation unit 600, FIG. 6 is a diagram showing points where a uniform radiation dose is exhibited with the compensation unit 600, and FIG. 7 is a diagram showing both a the lesion part 20 and the points uniformly irradiated with the radiation dose of FIG. 6.

As shown in FIG. 4, a radiation dose of a low energy level gradually decreases as a distance from the irradiation unit 500 increases. In the low energy level, significant difference in the radiation dose may be exhibited even though the distance is varied a little in units of mm. The low-energy radiation may show a low peak value or no peak values of the radiation dose depending on the distance as compared with that of high-energy radiation. However, the superficial lesion part 20 is irradiated for the purpose of treatment, and therefore a profile at which build-up of the skin surface 1 occurs may be used to calculate an adjustment value of the radiation dose.

In the meantime, the calculator 400 calculates the adjustment value of the radiation dose based on the radiation dose of the skin surface 1, i.e., the skin dose because individuals or tissue of parts are largely different in the radiation dose according to the depths from the skin surface 1, FIG. 5 shows the lesion part 20 on an uneven skin surface 1, and a relative distance from the end of the irradiation unit 500. The radiation dose may be largely varied depending on the distance, and thus parts P1 and P2 of the lesion part 20 may be different in the skin dose. Therefore, the calculator 400 calculate the radiation-dose adjustment value for the lesion part 20 in very small units by which the radiation-dose adjustment value is adjustable with respect to the radiation dose at a point of the minimum skin dose within the lesion part 20.

As shown in FIG. 6, the calculator 400 determines a radiation dose to be adjusted according to the coordinates in the treatment region. As described above, the point having the minimum skin dose in the lesion part 20 is selected as a reference skin dose SD, and attenuation values for other points having skin doses higher than the reference skin dose SD are determined according to coordinates.

The calculator 400 sets a high attenuation rate to be applied to a radiation dose for normal parts $P_3$ and $P_4$ other than the lesion parts $P_1$ and $P_2$ in the treatment region 10, thereby setting an attenuation value to minimize the radiation dose in the skin surface 1. It is ideally preferable that normal cells are not exposed to the radiation, and thus a radiation-dose attenuation value for the normal cells is set so high that the radiation can be sharply attenuated. In a plan view, when a simulation runs with a determined attenuation value, partial radiation attenuation is applied so that boundary coordinates 30 at points where the skin doses in the lesion part 20 have the reference skin doses SD can match 3D coordinates of an actual lesion part 20.

The calculator 400 generates the shape data of the compensation unit based on the attenuation values for the radiation doses according to coordinates. The shape of the compensation unit 600 may be determined based on boundary data about the adjustment of the radiation doses and partial thickness data corresponding to the attenuation values of the radiation doses. The boundary data may be obtained from the 3D scanning data and set to match the extracted boundary coordinates 30 of the lesion part 20 in the treatment region 10. In the partial thickness data, thickness $h_1$ and $h_2$ is determined based on the attenuation value determined according to coordinates. For example, the higher the attenuation value, the thicker the thickness.

FIG. 7 is a schematic view showing the radiation doses corresponding to parts when the compensation unit 600 made based on the shape data is applied.

As described above, a line of connecting the points, which have the reference skin dose SD when the attenuation values for the radiation doses according to the coordinates, matches the unevenness of the outer surface of the lesion part. Therefore, the radiation dose is adjusted in the lesion part 20 and uniformized throughout the skin surface. In the part other than the lesion part 20, the radiation dose is largely attenuated through the compensation unit 600 so that the radiation dose can be insignificant for normal cells. With this, the radiation dose is controlled to apply a uniform skin dose to the lesion part that occurs on an uneven or curved surface.

However, the foregoing shape of the compensation unit 600 is merely an example. Alternatively, the compensation unit 600 may have various shapes corresponding to the lesion part and the treatment region.

Below, an operation method of the low-energy radiation therapy system for the superficial lesion treatment will be described in detail with reference to FIG. 8.

Figure 8:
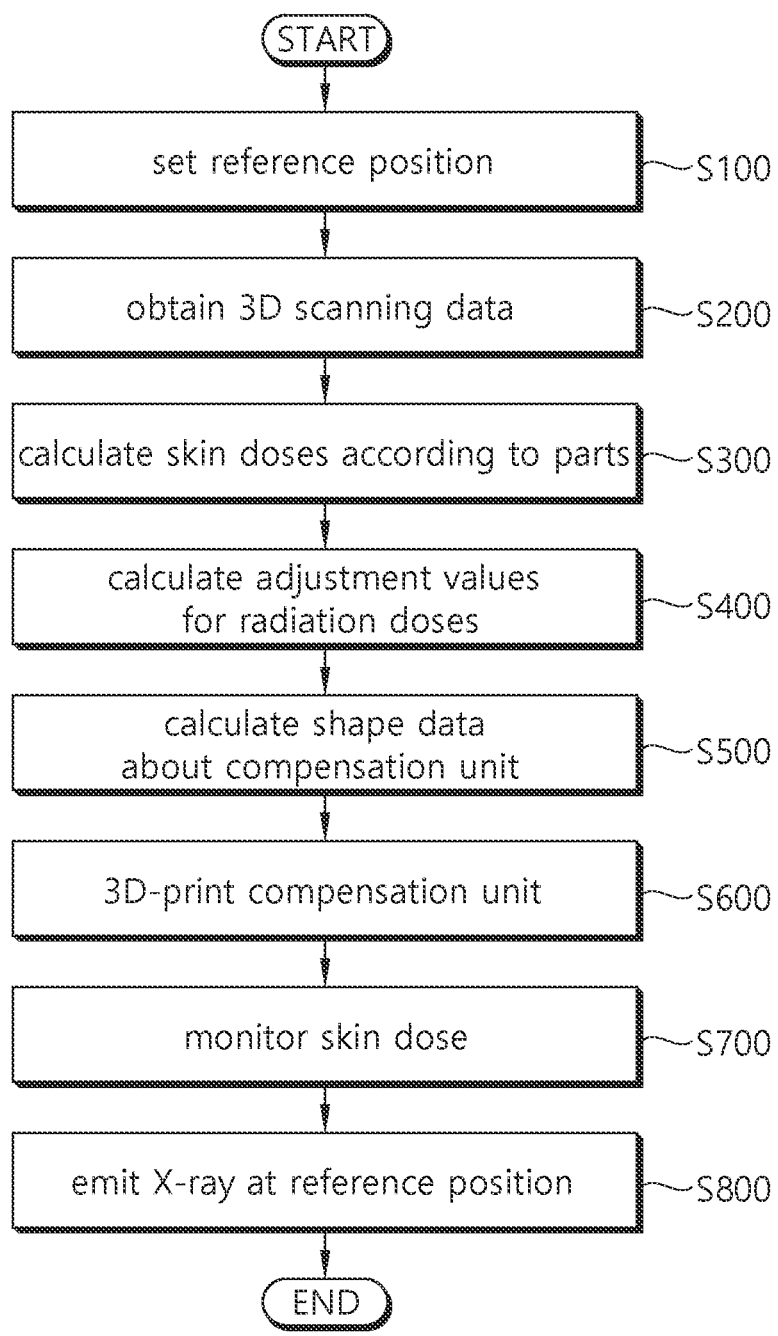
FIG. 8 is a flowchart of an operation method of a low-energy radiation therapy system for superficial lesion treatment according to another embodiment of the disclosure.

FIG. 8 is a flowchart of an operation method of a low-energy radiation therapy system for superficial lesion treatment according to another embodiment of the disclosure.

As shown therein, the operation method of a low-energy radiation therapy system for superficial lesion treatment according the disclosure may include steps of setting a reference position (S100), obtaining 3D scanning data (S200), calculating skin doses according to parts (S300), calculating adjustment values for radiation doses (S400), calculating shape data about a compensation unit (S500), 3D-printing the compensation unit (S600), monitoring the skin dose (S700), and emitting an X-ray at the reference position (S800).

The step of setting the reference position (S100) refers to a step of setting a position for the optical scanner 100 that applies 3D scanning to the lesion part 20 of a patient. For example, the reference position may be determined by a reference position value based on a sensing value of the position and posture of the scanner 100 that scans a part of a face while a patient lies.

The step of obtaining the 3D scanning data (S200) refers to a step of obtaining the 3D scanning data of the treatment region 10 including at least a part of the lesion part 20 through the optical scanner 100 at the reference position. In the step of obtaining the 3D scanning data, optical data based on visible light may be analyzed to extract data.

The step of calculating the skin doses according to the parts (S300) refers to a step of calculating the radiation doses on a skin surface based on a distance from the optical scanner 100 according to parts of the treatment region 10.

The step of calculating the adjustment values for the radiation doses (S400) refers to a step of calculating the adjustment values according to parts so as to uniformize the skin doses in an uneven lesion part 20. Here, when radiation is emitted to the lesion part 20 at the reference position, the adjustment values for the radiation doses of the other lesion parts 20 are determined so that the skin dose can converge into a low value. The adjustment value for the radiation dose is set to attenuate the radiation dose.

The step of calculating the shape data about the compensation unit 600 (S500) refers to a step of determining the shape of the compensation unit 600, which will be mounted to the end of the irradiation unit 500, based on the adjustment values for the radiation doses according to coordinates with regard to the lesion part 20. The boundary coordinates 30 of the lesion part 20 are extracted from the 3D scanning data, and the shape data about the three-dimensional compensation unit 600 is determined based on the adjustment values for the radiation doses according to the coordinates of the lesion part 20. The shape data of the compensation unit 600 may include thickness values in an irradiation direction determined based on the adjustment values of the radiation doses according to the coordinates of the lesion part 20. Meanwhile, the shape data may be converted by a parameter selected by a user. Here, the parameter may be selected differently according to the materials of the compensation unit 600.

The step of 3D-printing the compensation unit (S600) refers to a step of performing 3D-printing based on the shape data to make the compensation unit 600. In the 3D printing step, the 3D printing may be carried out as soon as the shape data is received.

The step of monitoring the skin dose (S700) refers to a step of verifying the radiation dose measured by actually emitting the radiation after mounting the compensation unit 600 to the end of the irradiation unit 500. If requirements for the skin dose are not satisfied, the step of measuring the skin doses according to parts to the step of 3D printing may be performed again.

The step of emitting the X-ray at the reference position refers to a step of emitting the X-ray at the reference position because the skin dose and the radiation dose are determined based on the reference position and the shape of the compensation unit 600 is determined. The emission of the X-ray may be based on low energy, and may specifically be carried out by generating the radiation within a range of 100 to 225 KV. The X-ray may for example be emitted for 40 to 55 seconds, and be repeated 10 to 20 times for the treatment.

As described above, the low-energy radiation therapy system for the superficial lesion treatment and the operation method thereof according to the disclosure have effects on securing rapidness and accuracy because a uniform skin dose is secured with regard to an uneven superficial lesion part and a compensation unit for adjusting a radiation dose is rapidly made by 3D printing and used. Further, there is an effect on minimizing a structure for shielding radiation because low energy is used in treatment.

The invention claimed is:

1. A radiation therapy system for superficial lesion treatment, comprising:
   an optical scanner configured to obtain 3D scanning data of a treatment region including a superficial lesion part;
   an irradiation unit configured to emit radiation to the treatment region;
   a calculator configured to calculate a skin dose, energy of the radiation, and adjustment values for radiation doses according to parts based on the 3D scanning data, and generate shape data about a compensation unit provided in an end portion of the irradiation unit based on the adjustment values for the radiation doses according to the parts; and
   a 3D printer configured to perform 3D printing based on the shape data to make the compensation unit,
   wherein the calculator is configured to generate the shape data about the compensation unit so that a skin dose of the lesion part can be uniformized in a state that the compensation unit is spaced part from the lesion part.

2. The radiation therapy system for the superficial lesion treatment according to claim 1, wherein the irradiation unit is configured to adjust the energy of the radiation.

3. The radiation therapy system for the superficial lesion treatment according to claim 2, wherein the irradiation unit is configured to vary the energy of the radiation within a range of 100 to 225 KV.

4. The radiation therapy system for the superficial lesion treatment according to claim 2, wherein the calculator is configured to calculate a distance between the irradiation unit and the treatment region based on the skin dose and the energy of the radiation.

5. The radiation therapy system for the superficial lesion treatment according to claim 4, further comprising a monitor configured to monitor the skin dose when the compensation unit is applied to the irradiation unit.

6. The radiation therapy system for the superficial lesion treatment according to claim 1, wherein the calculator is configured to generate the shape data so that the skin dose in the lesion part can converge into a predetermined range based on a minimum value of the skin dose.

7. The radiation therapy system for the superficial lesion treatment according to claim 1, wherein the calculator is configured to extract the 3D scanning data from an image obtained by scanning the lesion part through the optical scanner.

8. The radiation therapy system for the superficial lesion treatment according to claim 1, wherein the superficial lesion part comprises skin cancer.

9. An operation method of a radiation therapy system for superficial lesion treatment, the operation method comprising:
   setting a reference position as a scanning position of a scanner to scan a skin surface comprising a superficial lesion part;
   obtaining 3D scanning data about a treatment region by the scanner;
   calculating skin doses according to parts of the treatment region based on the 3D scanning data;
   calculating adjustment values for radiation doses according to parts based on the skin doses according to parts;
   calculating shape data about a compensation unit mounted to an irradiation unit based on the 3D scanning data and the adjustment values for the radiation doses according to parts;
   printing the compensation unit by a 3D printer; and
   emitting an X-ray to the treatment region at the reference position by an irradiation unit mounted with the compensation unit.

10. The operation method according to claim 9, further comprising performing monitoring by emitting the X-ray in a state that the compensation unit is mounted to the irradiation unit and measuring a radiation dose after the printing.

* * * * *